United States Patent [19]

Bauer et al.

[11] 4,433,076

[45] Feb. 21, 1984

[54] COATING AGENT FOR MEDICAMENTS AND METHODS FOR MAKING AND USING THE SAME

[75] Inventors: Kurt H. Bauer; Hermann Osterwald, both of Freiburg; Klaus Lehmann, Rossdorf; Dieter Dreher, Bickenbach, all of Fed. Rep. of Germany

[73] Assignee: Rohm GmbH, Darmstadt, Fed. Rep. of Germany

[21] Appl. No.: 328,486

[22] Filed: Dec. 8, 1981

[30] Foreign Application Priority Data

Dec. 24, 1980 [DE] Fed. Rep. of Germany ....... 3049179

[51] Int. Cl.³ .......................................... A01N 25/10
[52] U.S. Cl. ...................................... 523/342; 427/3; 424/33
[58] Field of Search .............. 427/3; 424/33; 523/342, 523/340

[56] References Cited

U.S. PATENT DOCUMENTS

| | | | |
|---|---|---|---|
| 2,800,463 | 7/1957 | Morrison | 523/342 X |
| 3,935,326 | 1/1976 | Groppenbacher et al. | 427/3 |
| 4,112,215 | 9/1978 | Boessler | 528/503 |

FOREIGN PATENT DOCUMENTS

| | | |
|---|---|---|
| 8780 | 3/1930 | European Pat. Off. . |
| 1814669 | 12/1968 | Fed. Rep. of Germany ........ 424/33 |
| WO80/00659 | 4/1980 | PCT Int'l Appl. ..................... 427/3 |

OTHER PUBLICATIONS

Technical Disclosures H–20 and H–23, Shin–Etsu Chemical Co., Ltd., Jan. 25, 1979 and Feb. 20, 1979.

*Primary Examiner*—Sam Silverberg
*Attorney, Agent, or Firm*—Curtis, Morris & Safford

[57] ABSTRACT

What are disclosed are methods for making a suspension suitable for use as a coating agent for medicaments by suspending a powder of certain vinyl copolymers in an aqueous solution or suspension of a plasticizer therefor, methods for converting such a suspension of copolymer in plasticizer into a film-forming solution or other extensively homogeneous phase, such suspensions and the film-forming conversion products thereof, and methods for coating medicaments with such suspensions and film-forming conversion products.

7 Claims, No Drawings

COATING AGENT FOR MEDICAMENTS AND METHODS FOR MAKING AND USING THE SAME

The present invention relates to a coating agent for medicaments and to methods for making and using the same.

A method for the preparation of medicament coatings which are resistant to stomach juices is known from the European patent application published as No. 8780. In this method, a water insoluble cellulose derivative is suspended in an aqueous solution of a plasticizer, boiling at a temperature above 100° C., for the cellulose derivative, and is applied to cores containing a medicament. The applied layer is then warmed, whereupon a portion of the water present in the suspension evaporates until the concentration of the dissolved plasticizer increases to the extent that the cellulose derivative is soluble therein. On cooling, the solution solidifies to form a hard coating. With reference to the technology of plastisols known in the synthetic resin arts, this method is designed as "thermogelation". Compared with the preparation of coatings from organic solutions, this method has the advantage that flammable or physiologically unacceptable solvents can be avoided. To be sure, pure aqueous dispersions of coating agents can also be used for the coating of medicament cores. However, these are not always satisfactory from the point of view of their ability to withstand storage, shelf-life, and ease with which they can be worked together with fillers and pigments.

Since the method of thermogelation is limited to cellulose derivatives, it does not offer the full range of possibilities which are available to the pharmacist in the preparation of medicament coatings from organic solutions of coating agents. For instance, heretofore, vinyl polymers, and above all acrylic polymers, which are used to a large extent in the form of organic solutions for coating medicaments, could not be used in a thermogelation method.

For the thermogelation method, powders of the binding material are employed in a grain size such that 95 percent by weight of the powder particles do not exteed a diameter of about 150 microns, and preferably do not exceed a diameter of 100 microns. Vinyl polymers which are resistant to stomach juices are easily accessible in this particle size by pearl polymerization methods. For example, a monomer mixture of unsaturated carboxylic acids and water insoluble vinyl monomers is suspended as droplets in an aqueous phase and the droplets are converted by polymerization into spherical polymer particles. Physiologically acceptable plasticizers for polymers of this type, which plasticizers have sufficient water solubility for use in a thermogelation method, for example polyethylene glycols or citric acid esters, are also available. Nevertheless, the thermogelation method cannot be carried out with these pearl polymers. Gelation does not occur and, as a result, there is no formation of a uniform film, free of pores, as is indispensible for producing a coating resistant to stomach juices on a medicament core.

Thus, the problem existed of finding vinyl copolymers useful in the thermogelation method and with which, just as for the case of cellulose derivatives, uniform closed coatings could be produced on medicament cores.

It has now been found that the copolymer powders prepared by spray drying according to U.S. Pat. No. 4,112,215, incorporated herein by reference, are suitable for this purpose. According to the present invention, the powders are employed in the form of a suspension in an aqueous solution or suspension of a plasticizer for the vinyl copolymer and are converted into a coating solution, paste, gel, or other extensively homogeneous phase by warming the resulting powder suspension. The vinyl copolymers will form a solution, paste, gel, or other extensively homogeneous phase on warming, or at least will form such as phase on warming if the water contained in the suspension is at least partially evaporated by the warming. The resulting phase is not always a completely homogeneous one, i.e. is not always a solution, since the central regions of the original latex particles sometimes remain undissolved. Nevertheless, the gelled outer regions of the polymer particles flow together to form a paste, or gel, or some other phase which is extensively homogeneous.

This phase, e.g. this solution of the coating agent, can then be applied hot to the medicament cores. However, the preferred embodiment of the present invention involves heating the suspension directly while it is present on the surface of the medicament cores, in this way to convert it into a film-forming coating phase, preferably a solution. In this case, the suspension can be so constituted that the resulting solution has the properties of a gel having little or no flow capability. On cooling, a hard, non-tacky, pore-free coating is formed.

According to the invention, the binders employed are powders which are obtained by spray drying an aqueous dispersion of a physiologically acceptable vinyl copolymer which is soluble in organic solvents and which is water-insoluble in one portion of the pH region between 1.5 and 8 and is water soluble or water swellable in another portion of this region. As water soluble unsaturated compounds present in the composition of the vinyl copolymer, ethylenically unsaturated polymerizable monocarboxylic acids or dicarboxylic acids or the salts, amides, hydroxyalkyl esters, monoalkylamino- or di-alkylamino-esters, or monoalkylaminoalkyl amides or dialkylaminoalkyl amides thereof, or the water soluble salts or quaternization products of the compounds mentioned above which contain an amino group, or vinyl pyrrolidone, or a N-vinyl imidazole can be used. Further, as one or more unsaturated compounds, also present as a component in the copolymer, are compounds forming a water insoluble homopolymer, such as styrene, vinyl acetate, an olefin, or, preferably, an alkyl ester of acrylic acid or of methacrylic acid having from 1 to 10 carbon atoms in the alkyl portion. The water soluble monomers preferably comprise from 5 to 80 percent by weight of the mono-ethylenically unsaturated, free-radically polymerizable compounds which form the vinyl copolymer. The amount of monomers which are difficultly soluble or are insoluble in water, and which comprise from 20 to 95 percent by weight of the vinyl copolymer, depends on the degree of hydrophilicity of the water soluble monomers which are copolymerized therewith.

The vinyl copolymers preferred for use are essentially formed from acrylic compounds and contain from 10 to 60 percent by weight of units of alpha, beta-unsaturated carboxylic acids, particularly acrylic acid or methacrylic acid, the remainder comprising units of alkyl esters of acrylic acid or methacrylic acid having from 1 to 8 carbon atoms in the alkyl portion. As a rule, these copolymers give coatings which are resistant to stomach juices, which are soluble or at least swell in the alkaline region of the intestine, and which are permeable to diffusion of the therapeutic agent.

In preparing the binder powder, the spray drying method is carried out with particular advantage in such a way that the polymer particles do not exceed the minimum film-forming temperature (MFT) of the polymer, which MFT is suitably greater than 80° C. These powders, preferred for use, are recognizable in that individual powder granules are comprised from loosely aggregated fine primary particles. This property is recognizable under a microscope, above all at a magnification of about 40-fold under a reflecting stereomicroscope. The granules can be divided practically without mechanical resistance with a needle, just like a loose snowball, whereby crumbled soft fragments adhere to the disintegrating tool. The diameter of the granules is generally less than 100 microns, preferably in the region between 20 and 60 microns while the primary particles of which they are composed are less than one micron in diameter.

The plasticizer obtained in the suspension must satisfy a series of requirements. Naturally, for pharmaceutical reasons it must be physiologically acceptable. It must be compatible with the vinyl copolymer to such a degree that the copolymer dissolves therein when warmed, and the resulting solution, which is more or less gel-like, must remain homogeneous on cooling and when stored for a long period. As a rule, the method demands that the plasticizer be soluble in the aqueous phase of the suspension to such a degree that a sufficient amount of the plasticizer is present for the gelation method together with an amount of solids which is technically acceptable. A solubility of 0.2 percent, at least on warming and preferably also at room temperature, is sufficient, even if the solubility is generally clearly above this value. Further, the plasticizer may not be volatile, or only slightly so, when warmed.

Plasticizers which fulfill these requirements and which are particularly suitable for use with vinyl copolymers comprising acrylic compounds are, for example, polyalkylene glycols having a molecular weight between 100 and 20,000, particularly those having 2 or 3 carbon atoms in each alkylene group. Polyethylene glycols are preferred, especially those having a molecular weight above 300. Copolymers of ethylene glycol and propylene glycol ("Pluronics")* are also suitable. Other plasticizers are the trialkylesters of citric acid and of acetyl-citric acid, particularly those wherein the alkyl groups have up to 4 carbon atoms each. In a broader sense, plasticizers may be used which are not wafter soluble and are emulsified in the aqueous suspension and which cause the conversion of the aqueous suspension into a film forming solution, paste, gel or other extensively homogeneous phase. Examples of these plasticizers, which are used in the form of a suspension, include copolymers of lower alkyl acrylates and lower alkyl methacrylates wherein the alkyl groups have up to 8, preferably up to 4, carbon atoms.

*"Pluronics" is a registered trade mark of BASF Wyandotte Corp.

The most suitable embodiment of the invention involves the use of a storage-stable prefabricated aqueous suspension which is applied to the medicament cores to be coated. The ratio of parts by weight of vinyl copolymer to plasticizing agent in the suspension is preferably in the range between 3:1 to 20:1. The solids content of the suspension is, for example, in the range from 5 to 30 percent by weight. Accordingly, the aqueous phase must consist of a solution of the plasticizing agent at a concentration of about 0.2 to 20 percent by weight.

The suspension can optionally contain further components such as water soluble thickening agents, emulsifiers, lubricants, fillers, pigments, and, optionally, also additional pharmaceutically active agents.

The suspension can be applied like other liquid coating agents in conventional coating kettles, film coating apparatus, or in fluidized bed apparatus, to dosage unit forms such as tablets, dragee cores, capsules, granules, or pellets, or to crystals or powders of the medicament, all of which are referred to herein as "medicament cores". Warming is effected, for instance, by blowing in warm air, which can have a temperature from about 40° C. to 100° C., whereby simultaneously water is evaporated from the suspension. At a surface temperature of 35° C. to 55° C., film forming occurs. In this way, pores and cavities in the surface of the dosage unit forms are filled in. For a uniform pore-free coating, 1 to 5 mg of dried binder substance are applied per square centimeter of surface in a layer thickness from 5 to 100 microns, which can be accomplished by applying the suspension in several portions.

Fundamentally, it is also possible to produce the film-forming suspension on the surface of the medicament itself. For example, the rolling dosage unit forms in a coating kettle are moistened with an aqueous solution or suspension of the plasticizing agent and the binder is strewn therein in the form of a dry powder, optionally mixed with other pulverized components. The water and the plasticizing agent can even be separately introduced and the powders then strewn in.

It should not remain unmentioned that the coated layer produced according to the present invention may be one of several layers which can, if desired, be prepared according to different methods, and need not be the outermost layer present on the end product. Such multiple coating are occasionally used for the purpose of directing release of the above agent in a particular desired manner.

A basic advantage of the invention lies in the possibility of preparing coated dosage unit forms, which earlier were prepared with organic coating solutions, with a coating agent which is free of any combustible solvent, without altering the composition and the properties of the coating, an achievement which is not otherwise readily possible, for example by the use of a film-forming aqueous dispersion.

A better understanding of the present invention and of its many advantages will be had by referring to the following specific Examples, given by way of illustration.

EXAMPLE 1

100 g of sprayed dried powder of a copolymer comprising 50 parts by weight of dimethylaminoethyl methacrylate, 25 parts by weight of methyl methacrylate, and 25 parts by weight of butyl methacrylate were suspended in a solution of 30 g of polyethylene glycol 3000 in 870 g of water by stirring with a magnetic stirrer and were then sprayed onto 2.5 kg of tablets having a diameter of 8 mm using a compressed air spray gun. The cores were previously brought to a temperature of 35° C. using warm air and were retained at this temperature during the spraying process. After an application time of 60 minutes, the tablets were completely covered with a shiny coating. The coating dissolved within 5 minutes in synthetic stomach juice at a pH of 1.8.

EXAMPLE 2

2 kg of tablet cores (7 mm in diameter, 140 mg in weight) were preheated to about 30° C. in a coating kettle having a diameter of 35 cm and rotating at a rate of 40 rpm by blowing in warm air at a temperature of 35° C. A compressed air spray gun having a nozzle opening of 0.5 mm was mounted over the kettle opening and 250 ml of a 10 percent aqueous solution of polyethylene glycol 6000 were introduced into the gun's storage vessel. Now, the tablets were alternately moistened by spraying in portions of about 15 ml of polyethylene glycol solution and dusted with about 5 g portions of a copolymer of equal parts of methyl methacrylate and methacrylic acid strewn in with a sieve. Altogether, in this manner about 250 ml of aqueous polymeric wax solution were sprayed and altogether 100 g of the aforementioned powder were introduced. The temperature of the tablet cores were held at about 35° C.–45° C. by the introduction of additional warm air. At the end, the film tablets were agitated for a further 5 minutes, whereby a shiny protective coating was produced. The coated tablets decomposed in water and synthetic stomach juice within about 15 minutes.

EXAMPLE 3

A suspension which contained a copolymer of 70 parts by weight of methyl methacrylate and 30 parts by weight of methacrylic acid as a binder was used in a coating process as in Example 1. Tablets were obtained which do not decompose within one hour in a synthetic stomach juice (according to the USP), but which dissolve after 30 minutes in synthetic intestinal juice having a pH of 7.5.

EXAMPLE 4

20 g of a sprayed dried powder of a copolymer comprising 50 parts by weight each of methyl methacrylate and methacrylic acid were suspended in 200 g of an aqueous emulsion of a polymer comprising 70 parts by weight of ethyl acrylate and 30 parts by weight of methyl methacrylate. The suspension was applied in a fluidized bed apparatus to 1 kg of etilefrin [D,L-1-(3-hydroxy-phenyl)-2-(ethylamino)ethanol] of pellets having a diameter of 0.8–1.2 mm. The air introduced had a temperature of 45° C. and the exhaust air had a temperature of 30°–35° C. The coated pellets of active material show retarded release of the active ingredient over a period of 2 hours in synthetic stomach juice.

EXAMPLE 5

100 g of sprayed dried powder of a copolymer of 50 parts by weight each of methylmethacrylate and methacrylic acid were suspended in 500 g of water and a solution of 30 g of a copolymer of 80 percent by weight of oxyethylene units and 20 percent by weight of oxypropylene units, having a average molecular weight of 1750, in 170 g of water was added with stirring. The mixture was stirred for 15 minutes and sprayed onto 2.5 kg of tablets having a diameter of 8 mm using a compressed air spray gun. The cores were preheated with warm air to 40° C. and were retained at 35°–40° C. during the spraying process. After an application time of 75 minutes, the tablets were completely covered by a shiny coating.

What is claimed is:

1. The method for making an aqueous suspension of a synthetic resin copolymer, which suspension is adaptable to use for forming a coating on a medicament core to form an orally-ingestible pharmaceutical dosage unit form, which method comprises suspending powder granules of said copolymer, formed by spray drying an aqueous dispersion of said copolymer, in an aqueous solution of a plasticizer for said copolymer or in an aqueous suspension of a plasticizer for said copolymer, said powder granules having a diameter between 20 and 60 microns and comprising loosely aggregated primary particles having a diameter of less than one micron, said copolymer comprising (a) 5 to 80 percent by weight of a water-soluble vinyl monomer selected from the group consisting of $\alpha$, $\beta$-unsaturated mono- and dicarboxylic acids and the amides, the hydroxy lower alkyl esters, the monoalkyl- and dialkyl-amino lower alkyl esters, and the quaternary ammonium salts of such amino lower alkyl esters of said acids, vinyl pyrrolidone, and vinyl imidazole; and (b) 95 to 20 percent by weight of a monomer selected from the group consisting of styrene, vinyl acetate, olefins, and alkyl esters of acrylic acid and methacrylic acid having 1 to 10 carbon atoms in the alkyl portion thereof; the relative amounts of monomers (a) and (b) in said copolymer being such that the minimum film-forming temperature thereof is greater than 80° C., said copolymer further being water-insoluble in one portion of the region between pH 1.5 and 8 and water-soluble or water-swellable in another portion of said region.

2. A method as in claim 1 wherein said copolymer comprises, as monomer component (a), a member selected from the group consisting of acrylic acid, methacrylic acid, acrylamide, methacrylamide, hydroxy lower alkyl acrylates and methacrylates, monoalkyl and dialkyl-amino lower acrylates and methacrylates, and quaternary ammonium salts of such amino lower alkyl acrylates and methacrylates.

3. A method as in claim 1 wherein said copolymer is suspended in a solution of a polyalkylene glycol plasticizer therefor.

4. A method as in claim 1 wherein the suspension of said copolymer in said plasticizer is warmed, whereby it is converted into a film forming solution, paste, gel or other extensively homogeneous phase.

5. A method as in claim 4 wherein water is evaporated from said suspension of copolymer in said plasticizer when said suspension is warmed.

6. An aqueous suspension of a synthetic resin copolymer, prepared by the method of claim 1.

7. A film forming solution, paste, gel, or other extensively homogeneous phase prepared by the method of claim 4.

* * * * *